United States Patent
Li et al.

(10) Patent No.: US 8,250,020 B2
(45) Date of Patent: Aug. 21, 2012

(54) METHOD AND SYSTEM FOR AUTOMATED ANALYSIS OF NUCLEAR MAGNETIC RESONANCE SPECTRA

(75) Inventors: Jiwen Li, Winterthur (CH); Abraham Bernstein, Ilchberg (CH); Bjoern Heitmann, Duebendorf (CH); Michael Fey, Andover, MA (US); Till Kuehn, Zurich (CH); Sandra Loss, Volketswil (CH); James Masse, Arlington, VA (US); Konstantin Pervushin, Zurich (CH); Oskar Schett, Uster (CH)

(73) Assignees: Bruker Biospin AG, Faellanden (CH); Universitaet Zuerich, Zuerich (CH)

( * ) Notice: Subject to any disclaimer, the term of this patent is extended or adjusted under 35 U.S.C. 154(b) by 534 days.

(21) Appl. No.: 12/461,834

(22) Filed: Aug. 26, 2009

(65) Prior Publication Data
US 2010/0063955 A1 Mar. 11, 2010

(30) Foreign Application Priority Data
Sep. 3, 2008 (EP) .................................. 08015519

(51) Int. Cl.
*G06N 5/00* (2006.01)
(52) U.S. Cl. ........................................... 706/52; 706/45
(58) Field of Classification Search .................... 706/52, 706/45
See application file for complete search history.

(56) References Cited

FOREIGN PATENT DOCUMENTS
WO WO 2007/023289 3/2007

OTHER PUBLICATIONS

Chow, et al., NMRES: An Artificial Intelligence Expert System for Quantification of Cardiac Metabolites from Phosphorus Nuclear Magnetic Resonance Spectroscopy, Annals of Biomedical Engineering, vol. 21, 1993, pp. 247-258.*
Blinowska, et al., Electroencephalography (EEG), Wiley Encyclopedia of Biomedical Engineering, 2006, pp. 1-15.*
Dunkel, et al. "Identification of organic molecules from a structure database using proton and carbon NMR analysis results". Journal of Magnetic Resonance, Academic Press, Orlando, FL, US, vol. 188, No. 1, Sep. 1, 2007, pp. 97-110.
Elyashberg, M.E. et al. "Computer-assisted structure verification and elucidation", Progress in Nuclear Magnetic Resonance Spectroscopy, Pergamon Press, Oxford, GB, vol. 53, No. 1-2, Jul. 8, 2008, pp. 1-104.

(Continued)

*Primary Examiner* — Wilbert L Starks
(74) *Attorney, Agent, or Firm* — Paul Vincent (57) ABSTRACT

A fully automatic, parameter free MR interpretation system is based on human logic emulation. Information is derived mainly from an MR spectrum with maximum confidence and in a similar way as a human expert. This is achieved by the combination of different expert systems that interpret certain MR spectral features as well as features from a proposed structure. The expert systems are dynamically linked to each other and the analysis is performed iteratively in all directions in a way that the expert systems can utilize all of the interpretations of all expert systems at all times. The expert system may generate not just a single result but rather lists of probability weighted hypotheses.

14 Claims, 2 Drawing Sheets

OTHER PUBLICATIONS

Golotvin S.S. et al. "Automated structure verification based on <1>H NMR prediction", Magnetic Resonance in Chemistry, John Wiley, Chichester, GB, vol. 44, No. 5, May 1, 2006, pp. 524-538.

Jens Meiler + Martin Will "Automated Structure Elucidation of Organic Molecules from $^{13}$C NMR Spectra Using Genetic Algorithms and Neural Networks", J. Chem. Inf. Comput. Sci. 2001, 41, 1535-1546.

Yunjun Wang + Oleg Jardetzky "Probability-based protein secondary structure identification using combined NMR chemical-shift data", Protein Science (2002), 11:852-861.

Ching-Cheng Wang, Jui-Hung Chen, Wen-Chung Lai, Woei-Jer Chuang, "2DCSi: identification of protein secondary structure and redox state using 2D cluster analysis of NMR chemical shifts", J. Biomol NMR (2007) 38:57-63.

\* cited by examiner

METHOD AND SYSTEM FOR AUTOMATED ANALYSIS OF NUCLEAR MAGNETIC RESONANCE SPECTRA

This application claims Paris Convention priority of EP 08 015 519.5 filed Sep. 3, 2008 the complete disclosure of which is hereby incorporated by reference.

BACKGROUND OF THE INVENTION

The invention concerns a method and a system for analyzing MR spectra. A method for automated interpretation of MR spectra is known from the article "Automated structure verification based on 1H NMR prediction", Magnetic Resonance in Chemistry, Volume 44 Issue 5, Pages 524-538, 2006.

In the state of the art MR spectra are processed in the peak analyzer which performs a peak picking routine which yields a peak list. The resulting peak list, that typically only contains the chemical shift values of the peaks, is then passed along to the multiplet analyzer which performs a multiplet analysis. The result of the multiplet analysis is a list of multiplets with their chemical shift positions, their multiplicity and their coupling constants. At some point during the analysis the expected structure is processed in the structure analyzer. The structure analyzer will predict a single list of multiplets from the structure. This multiplet list contains the predicted multiplet chemical shift positions, the predicted multiplicities with the predicted coupling constants. It may also contain error estimations on the predicted values for the chemical shift positions and the coupling constants. Then the two multiplet lists are matched in an iterative way where each predicted multiplet is matched to each multiplet resulting from the spectral analysis and the best matches are then counted. It is also possible to perform an overall analysis of all matches, where it might happen that a better overall match is found when the best matches for each single multiplet are not counted.

The known system then will produce a matching score where the overall matching factor and/or the single multiplet matching factors are passed along together with the resulting assignment, whereby the assignment specifies which atom or group in the molecule gave rise to which signal. In this way it is possible to assign a number of atoms to a certain area in the spectrum which then can be used to quantify the concentration of this compound in the solution. In some cases the matching score and the multiplet assignment is passed along to a result simplifier, which then applies a predefined empirical threshold to the matching score and thus decides whether the matching score is good enough to declare the expected molecular structure consistent with the spectrum or not.

However the result will only yield the correct concentration provided an expected structure is given, provided that the expected structure is correct, provided that the prediction of the list of multiples was correct and provided that the multiplet comparator matched the correct predicted multiplet to the correct experimental multiplet.

It is therefore an object of the invention to provide an optimized method and a system for automated analysis of MR-spectra which yields reliable information about concentration of a component of a sample without predicting an expected structure and which yields reliable interpretation of the NMR spectrum when an expected structure is supplied and thus declaring a spectrum consistent or inconsistent with the expected structure in a similar way a human expert would do this.

SUMMARY OF THE INVENTION

This object is achieved by a method according to the independent method claim. The method uses at least two expert systems which are feedback driven and which comprise embedded chemical and MR expert knowledge, whereby the data of the MR-spectrum are divided into interpreted data and non-interpreted data thereby forming at least one pair of interpreted and non-interpreted data, the method comprising the following steps:

a) assigning the whole data of the MR spectrum to the non-interpreted data;
b) feeding the pair of interpreted and non-interpreted data to the input of a first expert system;
c) generating new probability weighted pair of interpreted and non-interpreted data at the output of the expert system by extracting spectral information from the MR-spectrum and assigning probability factors to the extracted spectral information by means of MR expert knowledge of the expert system, and storing at least a part of the probability weighted data as new interpreted data;
d) feeding the new pair of interpreted data and non-interpreted data to a controller, the controller deciding either to stop the analyzing process or to feed the new pair of interpreted and non-interpreted data to the input of the first expert system or to an input of a further expert system; and
e) in case of not stopping the analyzing process, repeating steps c) and d), or
f) in case of stopping the analyzing process, either sending out a statement that the method could not interpret the data or sending out a resulting information comprising the pair of interpreted and non-interpreted data containing the highest information content compared to other pairs of interpreted non-interpreted data, whereby the new probability weighted pair of interpreted and non-interpreted data is at least one time fed to one expert system twice.

The inventive method optimizes the spectrum analysis by using expert systems, which mimic the spectroscopist's procedure for analyzing MR spectra of a sample such that the ratio of interpreted to non-interpreted data is maximized. The expert systems are feedback driven with embedded chemical and MR-expert knowledge for extracting spectral information in a probability weighted way. Thus the human chemist's dynamically renewed problem-solving strategy can be modeled. The extracted spectral information thereby comprising information which can be directly seen from the spectrum (e.g. chemical-shift, peak height and intensity . . . ) as well as interpretations of said information (e.g. atoms which may give rise to certain peaks, multiplets . . . ).

By feeding back the new interpreted and non interpreted data to the input of the expert system which generated said new interpreted and non interpreted data or to an earlier expert system their further decision making can be influenced. The decision whether the new interpreted and non interpreted data are fed back to the same experts system, to another expert system or the iteration process is stopped is done by the controller which therefore activates or deactivates the respective expert systems.

In the inventive method each expert system considers the whole spectral information, i.e. the new interpreted data as well as the new non interpreted data (comprising regions of the MR spectrum, which haven't been interpreted yet and therefore haven't been assigned to the interpreted data), and therefore is able to reconsider earlier hypotheses made by the same expert system or by another one. The new interpreted data therefore may refer to groups of data points (e.g. peaks, multiplets) of the MR-spectrum which have been assigned to non interpreted data before.

Because of this feedback procedure spectral information of an MR-spectrum can be derived even without knowledge of an expected molecular structure.

In step c) of the inventive method preferably more than one new probability weighted pair of interpreted and non-interpreted data is generated at the output of the expert system.

In a variant in step c) the probability weighted extracted spectral information are stored as new interpreted data only in case that the corresponding probability factor exceeds a previously defined threshold. Thus the number of hypotheses can be limited.

In a highly preferred variant of the inventive method the new pair of interpreted and non-interpreted data stored in step c) is at least one time fed back to the input of the same expert system, in which said interpreted and non-interpreted data has been stored, the expert system thereby deriving information that have high probability factors in order to influence further decision making. The new interpreted data can then be revised by the same expert system in view of different parameters.

Advantageously for the very first assignment of probabilities to the extracted spectral information from the MR-spectrum an initial guess for these probabilities are made, using the embedded chemical and MR expert knowledge.

In a preferred variant one of the expert systems is a peak identifier and the generation of the new probability weighted pair of interpreted and non-interpreted data is carried out by a peak picking routine, whereby peak hypotheses are made and stored as new interpreted data.

In this case the extracted spectral information can be, but are not limited to, chemical shift information and/or integral information and/or line shape information.

It is also advantageous if one of the expert systems is a multiplet identifier, whereby the generation of the new probability weighted pair of interpreted and non-interpreted data is carried out by grouping peak clusters into possible multiplets and assigning probabilities to these multiplet hypotheses, whereby said multiplet hypotheses are stored as new interpreted data.

Most preferably the number of atoms is assigned to the multiplet hypotheses.

By using a multiplet identifier the extracted spectral information can be, but are not limited to, chemical shift information and/or line shape information and/or integral information and/or multiplet patterns and/or couplings between different multiplets and/or structural information and/or information about the number of atoms that give rise to certain multiplets in the spectrum and/or information about spectral artifacts and/or information about spectral signals which do not originate from the main compound.

Particularly preferred is a variant in which after step d) the new pair or interpreted and non interpreted data is fed to the input of another expert system which is a structure analyzer and spectra matching system, whereby the structure analyzer and spectra matching system predicts spectral parameters from a given expected molecular structure, assigns probability factors to said predicted spectral parameters, generates a new probability weighted pair of interpreted and non-interpreted data by analyzing the consistency of the pair of interpreted and non interpreted data, which has been fed from previous expert system, with the predicted spectral parameters with their assigned probability factors, and feeds the new pair of interpreted data and non-interpreted data to the controller.

The invention also concerns a system for analyzing MR spectra with the above described method, the system comprising:

an initializer for assigning data of an MR spectrum to a category interpreted data or to a category non interpreted data, whereby the initializer comprises an input for receiving MR data, at least two expert systems, each having an input for receiving interpreted and non interpreted data and an output for passing probability weighted new interpreted and non interpreted data, a controller with an input for receiving the new interpreted and non interpreted data from the expert systems, with an output for feeding the new interpreted and non interpreted data to one of the expert systems and with a further output for sending out a statement with resulting information, whereby the input of each expert system is connected to the initializer, to the output of each expert system and to the output of the controller, and whereby the input of the controller is connected to the output of each expert system.

An expert system for the purpose of this invention comprises expert knowledge for a special analysis routine and rules which are associated with said expert knowledge. The expert system used in the present invention further considers probabilities and therefore approaches the problem to be solved similar to a human being.

Different interpretations (hypotheses) of the MR-spectrum are considered, rated by assigning probability factors and are continued in further processing. The assigned probabilities can vary during the analysis process, for example because of information which has been extracted by different analysis routines after assigning the probability factors to the hypotheses. The expert system considers the earlier ratings as well as the newly received information and therewith may adapt the probability factors accordingly. I.e. the hypotheses are looped back and reconsidered from a different point of view therewith implying human logic emulation.

In a preferred embodiment of the inventive system one of the expert system is a peak identifier and another of the expert system is a multiplet identifier.

Further it is advantageous if a further expert system is provided, which is a structure analyzer and spectra matching system, whereby the structure analyzer and spectra matching system has a further input for receiving expected molecular structure information.

DESCRIPTION OF THE PREFERRED EMBODIMENT

Figure 1:
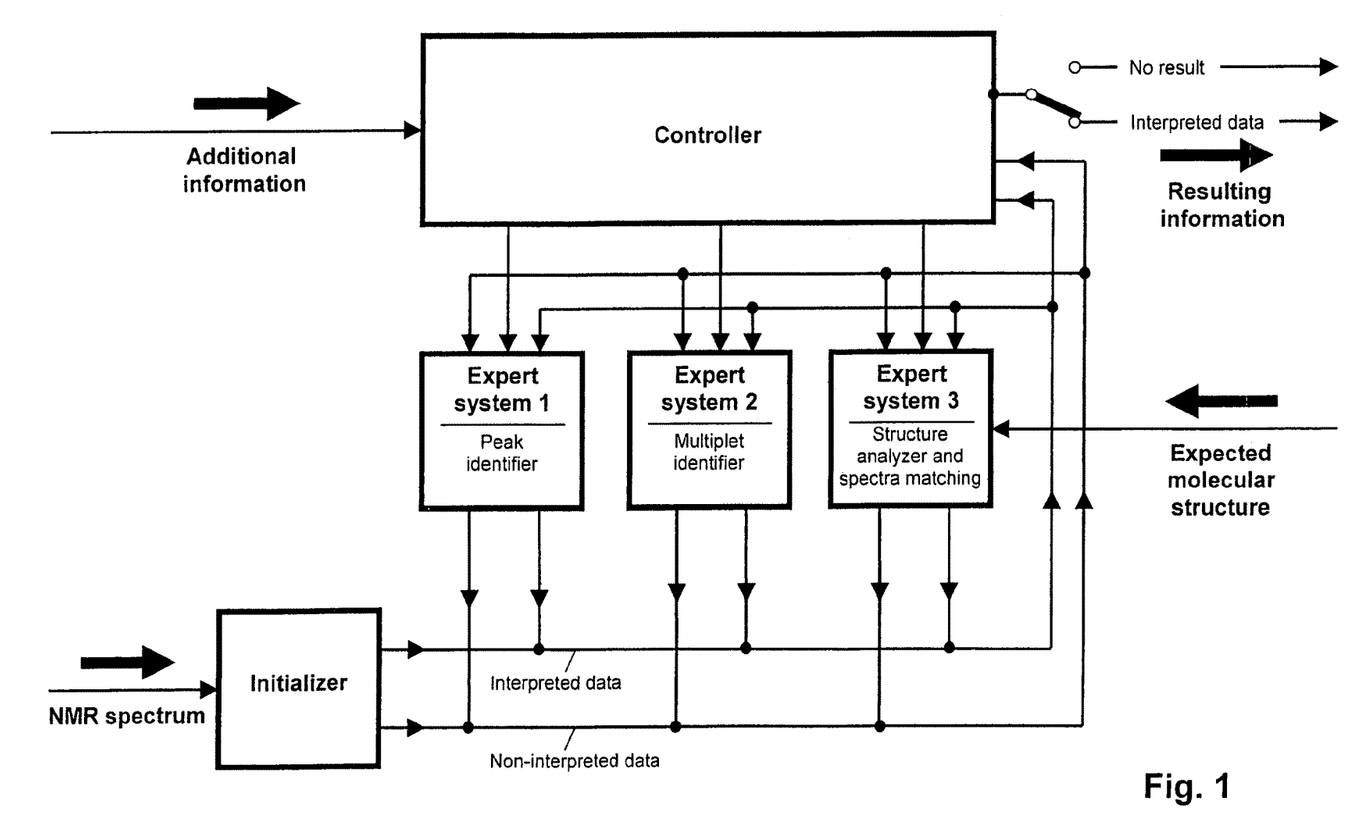
FIG. 1 shows a preferred embodiment of the inventive system.

The inventive method comprises a first step in which an MR spectrum is sent to an initializer where the MR spectrum is divided into two sets of data, the "interpreted data" and the "non-interpreted data", referred to as a "initial pair of interpreted and non-interpreted data", as shown in FIG. 1. The sum of initial interpreted and non-interpreted data is equal to the original MR spectrum. The analyzing process begins with an initial step by generating an initial pair of data, where the non-interpreted data are set equal to the original MR spectrum and all values of the interpreted data are set equal to zero, i.e. no data point of the MR spectrum is assigned to the interpreted data at the beginning of the analyzing process.

The aim of the inventive method is to optimize spectra analysis by maximizing the amount of interpreted data and thus minimizing the amount of non-interpreted data. This goal is achieved by applying a dynamically renewed problem-solving strategy of the chemist and emulated human logic to an analyzing method.

During the first iteration process a first expert system (peak identifier) receives the initial pair of data from the initializer. The peak identifier then performs an initial peak picking routine—such as for example a simple search for maxima with a noise threshold—in order to generate an initial list of probable peaks, whereby probabilities are assigned to each detected peak by performing educated guesses. These probabilities can be evaluated using the internal knowledge of the peak identifier (for example peaks with low intensities may be assigned with low probabilities, etc). This first spectral information comprises groups of data points of the MR spectrum (hypothesis area) for which a hypothesis has been made as well as the hypothesized peaks within the hypothesis area and is stored as new interpreted data. The regions which could not be assigned to peaks are stored as new non-interpreted data.

This new pair of interpreted and non-interpreted data (with the spectral information stored as interpreted data) is then fed to a controller which may either decide to stop the iteration and the analysis process completely and yield a statement that further analysis on this MR spectrum is impossible. (This may be the case for example when the controller has evaluated or received some additional information and decides that any further analysis of the MR spectrum is impossible since e.g. some of the MR experimental parameters that where used to acquire the MR spectrum where inappropriate.) Or the controller decides to loop the pair of interpreted and non-interpreted data back into the peak identifier. The peak identifier can then for example perform a line shape analysis on the stored peak hypothesis areas and for example define an average peak-line shape. It then can also reassign the probabilities of the hypothesized peaks e.g. in a way that peaks that deviate from the average peak-line shape receive a lower probability than the ones that are close to the average peak-line shape. These new peak hypotheses with the corresponding new information of the peak line shape, the intensity and the integrals as well as the probabilities assigned to each peak are again stored as new interpreted data and the rest of the MR spectrum is assigned as new non-interpreted data.

It may happen that more than one different peak hypothesis lists is able to explain the MR spectrum, so that the peak identifier may write more than one pair of new interpreted non-interpreted data to the output of the peak identifier.

The new interpreted and non-interpreted data go back into the controller which can then decide either to send the data back again to the peak identifier where the peak hypotheses may even be refined further (e.g. peaks that had been assigned to high probability factors since they match the average peak-line shape very well now may get assigned to lower probability factors because they either have very low intensities or they appear in areas where common impurities are expected).

Alternatively the controller decides to stop the iteration and the analysis of the MR spectrum completely and send out a statement that the optimizing method could not interpret the data. This may be the case for example when too many or too few peaks for a reliable analysis have been found by the peak identifier.

The controller may also decide to hand on the interpreted and non-interpreted data to the next expert system—in this case the multiplet identifier. This may happen for example when there has been no significant change in the interpreted and non-interpreted data after the last iteration as compared the iteration before.

The multiplet identifier receives the new interpreted and non-interpreted data, whereby the interpreted data received by the multiplet identifier also comprise a peak hypothesis lists which include probabilities for peak positions, peak shapes and possibly more information such as peak intensities or peak integral values. Provided with this information and expert knowledge on multiplet interpretation, the multiplet identifier now groups peak clusters into possible multiplets and assigns probabilities to these multiplet hypotheses. Initially all theoretically possible peak combinations are grouped into multiplets and probabilities are assigned to the respective solutions initially using the knowledge of the expert system for an educated guess.

The resulting new interpreted data then comprise these multiplet hypothesis lists and new pairs of interpreted and non-interpreted data can then be sent back into the multiplet identifier by the controller in a similar way as described above for the peak identifier. The controller can also decide to stop any further analysis of the MR spectrum as described above.

Provided the controller decides to reiterate the new interpreted and non-interpreted data through the multiplet identifier, the initial guesses for the assignments of multiplets may be re-evaluated and new probabilities may now be assigned. This may for example be the case, when a multiplet which was initially quite unlikely now becomes more likely since it's coupling constant and integral makes it a very likely coupling partner to another well defined multiplet that initially had a high probability assigned to it.

During this analysis, hypotheses concerning the numbers of atoms which may give rise to a specific multiplet will also be assigned to the new interpreted data and will be reconsidered in future iterations. This can be achieved in the multiplet identifier using its embedded expert knowledge. E.g. the ratios of the integrals between different multiplets can be evaluated along with a consideration of their coupling properties and multiplicities as well as their chemical shift positions within the spectrum. In this way it is possible to unambiguously formulate hypotheses of the numbers of atoms that give rise to a certain multiplet in the spectrum without any knowledge of the molecular structure of the sample.

All these aspects will result in one or more new pairs of interpreted and non-interpreted data which may yet again go through the same expert system or where the controller decides to send it on to another expert system.

The controller may even decide to send the interpreted and non-interpreted data back into the previous expert system—in this case the peak identifier—which may use the additional information derived from the multiplet identifier to reassign peak probabilities in the peak hypothesis lists. This may for example be advantageous when a peak hypothesis becomes more likely if it is part of a very likely multiplet even though the specific peak initially had a low ranking because—for example—its intensity was too low.

This again results in new pairs of interpreted and non-interpreted data, which go back through the peak identifier until the controller decides to send it on to the multiplet identifier again. In the multiplet identifier the probabilities for the multiplet hypothesis lists may again be reassigned. For example it may be that the peak identifier yielded the information that an initially likely multiplet required a high probability of a certain peak. But running the hypothesis for this peak through the peak identifier yielded only a very low probability for a peak at the expected position since—for example—its peak-line shape deviated too much from the average. In this example, the probability for this specific multiplet will then be lowered in the multiplet identifier.

The controller decides when to stop this iteration and when to move the interpreted and non-interpreted data on to the next expert system, in the shown example the structure analyzer and spectra matching. Here again the decision of the controller to move on the interpreted and non interpreted data can be based for example on the requirement that the interpreted and non interpreted data stay consistent after a few iterations.

In the structure analyzer and spectra matching, an expected molecular structure (external input) is analyzed and hypotheses for expected spectral parameters—for example multiplets with certain chemical shift hypotheses, coupling constant hypotheses and peak-line shape hypotheses etc.—are generated using the expert knowledge within this expert system. These predicted spectral parameters get also assigned ranges and probabilities and are grouped into hypothesis lists similar to the hypothesis lists in the interpreted data of the MR-spectrum. These hypothesis lists are then compared to the interpreted data so far derived from the spectrum using the peak identifier and the multiplet identifier. During this process the pairs of interpreted and non interpreted data may become refined or redefined and the controller decides whether they are iterated back through the previous expert systems.

Based on this now derived additional information the probabilities in the multiplet hypotheses or even in the peak hypotheses may be rearranged. If the system then ends up with a solution of a high probability for peaks and multiplets in the spectrum that correlates with the probabilities for peaks and multiplets originating from the expected molecular structure, then the expected molecular structure and the spectrum are considered consistent and the structural features of the expected molecular structure are directly assigned to spectral features of the MR spectrum. In the case the controller detects consistency in the interpreted and non interpreted data it will send out final new interpreted data with the highest information content as the resulting information. The final new interpreted data comprise all interpreted peaks, multiplets, integrals, the numbers of atoms that gave rise to certain multiplets and other spectral features and also an assignment of these spectral features to the respective atoms or groups in the expected molecular structure. In this case the expected structure is consistent with the analyzed MR spectrum. This is an optimized result of the inventive analyzing method.

In the case that the controller does not detect consistency in the interpreted and non interpreted data in the final step, but so far the MR data has been considered interpretable, the controller also sends out the final new interpreted data with the highest information content as the resulting information. This also contains all interpreted peaks, multiplets, integrals, number of atoms that gave rise to certain multiplets and other spectral features of the MR spectrum. But in this case the expected structure is not consistent with analyzed MR spectrum and no assignments of atoms or groups to spectral features can be made. This can also be a result of the analyzing method.

In case no expected molecular structure is available, the iteration through the last expert system—the structure analyzer and spectra matching—is omitted. Then the controller simply presents the last new interpreted data with the highest information content as the resulting information which also contains all interpreted peaks, multiplets, integrals, number of atoms that gave rise to certain multiplets and other spectral features of the MR spectrum. This can also be a result of the optimizing method and it can for example be used to quantify the amount of compound that gave rise to the analyzed MR spectrum without the knowledge of its chemical structure.

The controller may also use additional information which may for example originate from other spectroscopic results or from the knowledge of the synthesis pathway or from the knowledge of the MR experimental details for the examined sample that gave rise to the analyzed MR spectrum. The additional information may influence the decision making of the controller. E.g. when additional uv-, ir- , ms- or x-ray information is available on the analyzed sample, that states that the sample and the proposed structure are not consistent, then the controller might decide to run more iterations or raise certain thresholds in order to perform the MR analysis.

Figure 2:
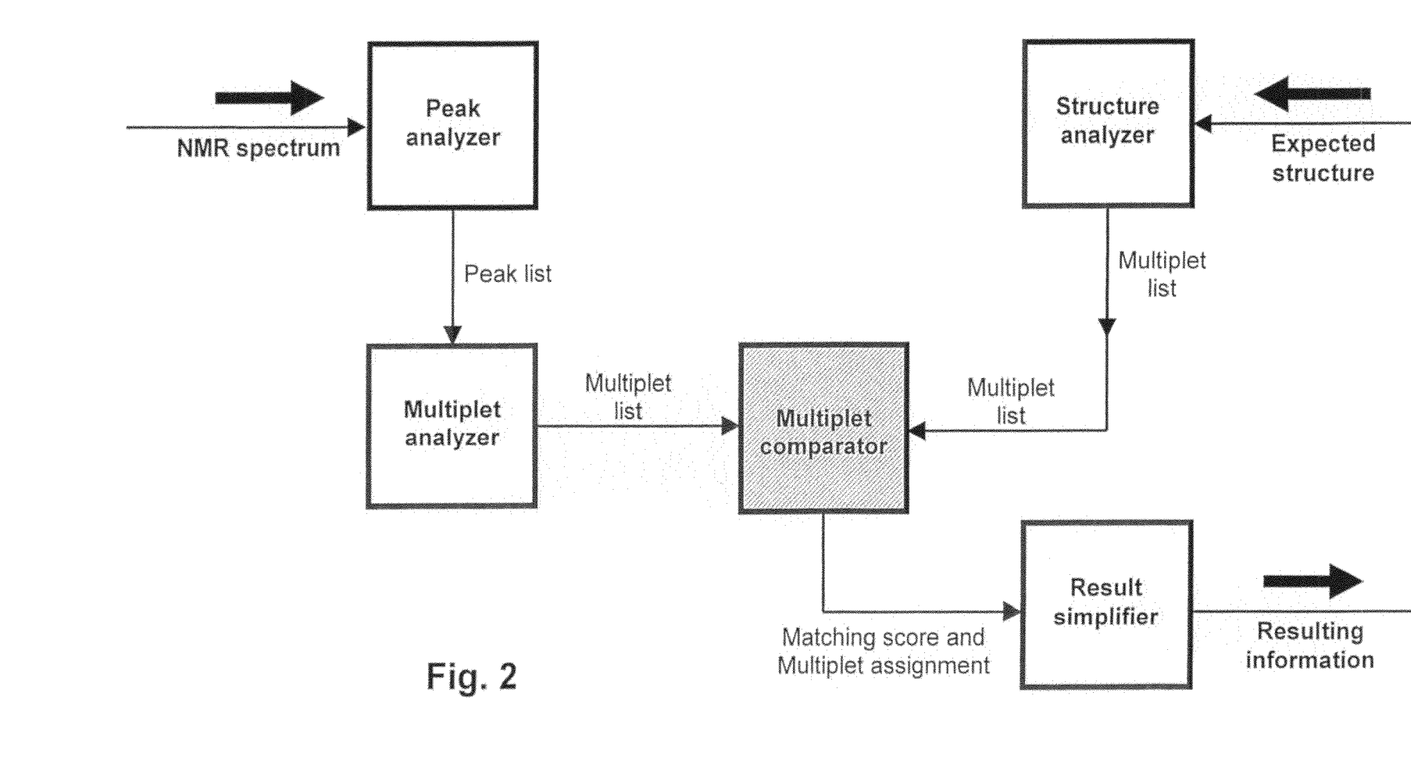
FIG. 2 shows a system for analyzing MR spectra according to the state of the art.

In contrast to the known method (shown in FIG. 2) the inventive method uses human logic emulation in a way that each result obtained from any expert system can be revised by any expert system. Therefore the flow of the data interpretation is not a one way direction but additional information can be looped back, so that all expert systems can use any additional information to refine the result. This looping back can be carried out between different expert system but is also possible that the results of one expert system are even fed to this same expert system again, which may alter and improve the interpretation of the data. The state of the art methods as shown in FIG. 2 however are one-directional and do not allow looping back of additional information into the same or previous modules.

In contrast to the known method the inventive method uses probability based approaches for all its processes. This means that even intermediate results are probability weighted and different intermediate results are possible and can be further considered. The current solutions do not use probabilities in their intermediate result generation for the spectra interpretation. Instead, often merely rule based methods are used which only consider rules and their exceptions, leading to only one single solution for each module. All other possible solutions are lost and will not be further considered. For example the multiplet analyzer of a state of the art system will assign exactly one multiplet type to a group of peaks which will be the only one that is further considered in the process. Whereas the inventive method is able to generate a list of multiplet hypotheses for this group of peaks and will assign probabilities to them and all or at least the most likely hypotheses will be considered in the further progress of the spectral analysis.

Compared to the analyzing methods known from the state of the art, the inventive method yields more information. For example the peak identifier of the inventive system yields more information than the respective peak analyzer in the conventional process: The conventional peak analyzer yields a peak list that typically contains the chemical shift values of the peaks—possibly along with the intensity of this data point, whereas the peak identifier of the inventive method may yield several possible interpretations with probabilities assigned to them and which contain the parameters as the chemical shift of the peak, its intensity, its integral value and its line shape.

The multiplet analyzer of the conventional method yields one list of multiplets with their chemical shift position of the multiplets, the multiplicity, the coupling constants and the position of the peaks within the multiplets, whereas the multiplet identifier of the inventive method may yield several possible interpretations on the same spectrum where all of them contain probabilities for the following parameters: the chemical shift position of the multiplet, the multiplicity, the coupling constants, the position of the peaks within the multiplet, their intensities, the integral of the multiplet, hypotheses for possible coupling partners for this multiplet in the spectrum, hypotheses on the number of atoms that gave rise to this multiplet and the probability whether this multiplet may belong to the main component or if it belongs to impurities or solvents or is an experimental artifact.

With the inventive method the spectral analysis is directly done on the experimental spectrum from the very beginning, i.e. the whole spectrum is considered at any time during the analyzing process, and thus the inventive method yields a wealth more information than the current analysis. This means for example, that the inventive method can deal with impurities in the sample since the signals arising from these impurities or experimental artifacts can be identified during the spectral analysis. This is a fundamental advantage of the inventive method over the current approaches. The information on artifacts and impurities can be used in the process where the predicted MR parameters of the expected molecular structure are assigned to the identified multiplets in the spectrum. The advanced spectral interpretation of the inventive method will prevent that a predicted multiplet from the expected molecular structure is matched and assigned to an impurity peak that a human expert would clearly identify as such. This is a common problem of the current technology.

Intrinsically the multiplet identifier of the inventive method can distinguish multiplets that belong to the main component from multiplets that do not belong there. This is impossible with all other approaches that have to rely on lists of common impurities and their MR properties. But these lists will never be complete and will never be able to cover all possible side products of chemical reactions. Also experimental artifacts can not be handled by state of the art methods.

The information on artifacts and impurities gathered by the inventive method can be directly used for an estimation of the purity of the sample as a ratio between the signal integral values originating from assigned artifacts and impurities on one side and the total integral of all signals in the spectrum on the other side.

In the described inventive method a full spectral analysis is done in a very similar way as a human expert interprets a spectrum—even before any information on the proposed chemical structure is used. This means that the spectral information can be used independently from predicted structural information. Practically, this means that it is possible to for example quantify the concentration of the main compound in the spectrum even if the proposed structure does not correspond to the main compound in the spectrum or even if the main compound's structure is not known. This is not possible with any other system which relies for quantification on the correct matching of the proposed structure to the spectrum.

Further the described inventive method uses a controller which may stop the analysis of the data at any time. This may for example be the case when the supplied MR spectrum is non-interpretable due to too many or too prominent experimental artifacts. It may also be that spectral information is not sufficient to present a confident result. Such a procedure, which stops the interpretation of certain data and rather not dare to present a result, increases the confidence in the results that are actually generated, i.e. the optimizing method knows its limitations. This is not possible with the current design which always will produce a result which then can only be revised in a very rudimentary way at the end of the analysis in the result simplifier that simply applies a threshold to the matching score.

After all the inventive system constitutes a fully automatic, parameter free MR interpretation system based on human logic emulation. The inventive method derives information mainly from an MR spectrum, in particular NMR spectrum, with maximum confidence and in a similar way as a human expert. The final result may include
- the concentration of the main component in the sample that gave rise to the MR spectrum (e.g. 8.3 mM),
- an estimation on the purity of this main component (e.g. 92% pure),
- a statement whether or not a proposed chemical structure is consistent with the identified main component in the MR sample,
- a statement that parts or all of the analysis of this particular sample could not be performed due to poor data quality or not enough data.

This can be achieved by the combination of different expert systems which interpret certain MR spectral features as well as features from a proposed structure. The expert systems are dynamically linked to each other and the analysis is performed iteratively in all directions in a way that the expert systems can utilize all of the interpretations of all expert systems at all times. The expert systems may generate not just a single result but rather lists of probability weighted hypotheses.

This procedure mimics a human expert, who will also review his previous results and reevaluate his findings depending on already evaluated results. This loopback procedure is implemented in the method as a substantial tool to improve the result and define a criterion to terminate the process.

We claim:

1. A method for analyzing an MR spectrum or a nuclear magnetic resonance spectrum, the method using at least two expert systems having chemical and MR-expert analysis tools, the method comprising the steps of:
   a) initially characterizing all data in the MR spectrum as non-interpreted data;
   b) feeding, following step a), the non-interpreted data to an input of a first expert system;
   c) analyzing, in the first expert system, a spectral content of the non-interpreted data of step a) with regard to first specific spectral features thereof which the first expert system is structured to assess and reassigning that non-interpreted data into newly interpreted data and newly non-interpreted data, thereby associating a probability weighting to both the newly non-interpreted and the newly interpreted data;
   d) feeding the newly interpreted data and the newly non-interpreted data to a controller, the controller structured to evaluate progress in reassigning non-interpreted data into interpreted data and deciding, in dependence on that progress, either to stop an analyzing process or to feed the interpreted and the non-interpreted data back to the input of the first expert system or to an input of a second expert system;
   e) in the event that the controller decides to feed the interpreted and non-interpreted data back to the first expert system, re-analyzing, in the first expert system, a spectral content of the non-interpreted and interpreted data with regard to the first specific spectral features thereof and re-assigning the non-interpreted data and interpreted data into newly interpreted data and newly non-interpreted data, thereby associating a new probability weighting to both the interpreted data and the non-interpreted data;
   f) in the event that the controller decides to feed the interpreted and non-interpreted data to the second expert system, re-analyzing, in the second expert system, a spectral content of the non-interpreted and interpreted data with regard to second specific spectral features thereof which the second expert system is structured to assess and re-assigning the interpreted data and the non-interpreted data into newly interpreted data and newly non-interpreted data, thereby associating a new probability weighting to both the non-interpreted and the interpreted data;

g) repeating step d); and h) in case of stopping the analyzing process, either sending out a statement that the method could not interpret the data or sending out a resulting information comprising a pair of interpreted and non-interpreted data containing a highest information content compared to other pairs of interpreted and non-interpreted data, wherein a new probability weighted pair of interpreted and non-interpreted data is fed at least twice to one of the first and the second expert systems.

2. The method of claim 1, wherein a plurality of new probability weighted pairs of interpreted and non-interpreted data are generated at an output of a respective expert system.

3. The method of claim 1, wherein probability weighted extracted spectral information are stored as new interpreted data only in case an associated probability factor exceeds a previously defined threshold.

4. The method of claim 1, wherein for a first assignment of probabilities to extracted spectral information from the MR-spectrum, an initial guess for these probabilities are made using chemical and MR-expert knowledge resident in the first expert system.

5. The method of claim 1, wherein said first expert systems is a peak identifier and generation of a new probability weighted pair of interpreted and non-interpreted data is carried out by a peak picking routine, wherein peak hypotheses are made and stored as new interpreted data.

6. The method of claim 5, wherein extracted spectral information comprises chemical shift information, J-coupling information, integral information, and/or line shape information.

7. The method of claim 1, wherein said second expert systems is a multiplet identifier, wherein generation of a new probability weighted pair of interpreted and non-interpreted data is carried out by grouping peak clusters into possible multiplets and assigning probabilities to these multiplet hypotheses, wherein the multiplet hypotheses are stored as new interpreted data.

8. The method of claim 7, wherein a number of atoms is assigned to the multiplet hypotheses.

9. The method of claim 7, wherein extracted spectral information is chemical shift information, shape information, integral information, multiplet patterns, couplings between different multiplets, structural information, information about a number of atoms that give rise to certain multiplets in the spectrum, information about spectral artifacts and/or information about spectral signals which do not originate from a main compound.

10. The method of claim 1, wherein a new pair of interpreted and non-interpreted data is fed to an input of another expert system which is a structure analyzer and spectra matching system, wherein the structure analyzer and spectra matching system
  predicts spectral parameters from a given expected molecular structure,
  assigns probability factors to predicted spectral parameters,
  generates a new probability weighted pair of interpreted and non-interpreted data by analyzing consistency of the new interpreted and non-interpreted data with the predicted spectral parameters with their assigned probability factors, and
  feeds the new pair of interpreted and non-interpreted data to the controller.

11. A system for analyzing an MR spectrum or a nuclear magnetic resonance spectrum, the system using at least two expert systems having chemical and MR-expert analysis tools, the system comprising:
  means for initially characterizing all data in the MR spectrum as non-interpreted data;
  means for feeding the non-interpreted data to an input of a first expert system;
  means for analyzing, in the first expert system, a spectral content of the non-interpreted data with regard to first specific spectral features thereof which the first expert system is structured to assess and reassigning that non-interpreted data into newly interpreted data and newly non-interpreted data, thereby associating a probability weighting to both the newly non-interpreted and the newly interpreted data;
  means for feeding the newly interpreted data and the newly non-interpreted data to a controller, the controller structured to evaluate progress in reassigning non-interpreted data into interpreted data and deciding, in dependence on that progress, either to stop an analyzing process or to feed the interpreted and the non-interpreted data back to the input of the first expert system or to an input of a second expert system;
  means, in the event that the controller decides to feed the interpreted and non-interpreted data back to the first expert system, for re-analyzing, in the first expert system, a spectral content of the non-interpreted and interpreted data with regard to the first specific spectral features thereof and re-assigning the non-interpreted data and interpreted data into newly interpreted data and newly non-interpreted data, thereby associating a new probability weighting to both the interpreted data and the non-interpreted data;
  means, in the event that the controller decides to feed the interpreted and non-interpreted data to the second expert system, for re-analyzing, in the second expert system, a spectral content of the non-interpreted and interpreted data with regard to second specific spectral features thereof which the second expert system is structured to assess and re-assigning the interpreted data and the non-interpreted data into newly interpreted data and newly non-interpreted data, thereby associating a new probability weighting to both the non-interpreted and the interpreted data;
  means for iteratively passing the non-interpreted data and the interpreted data from the first and second expert systems to the controller; and
  means, in case of stopping the analyzing process, for either sending out a statement that the data could not be interpreted or for sending out a resulting information comprising a pair of interpreted and non-interpreted data containing a highest information content compared to other pairs of interpreted and non-interpreted data, wherein a new probability weighted pair of interpreted and non-interpreted data is fed at least twice to one of the first and the second expert systems.

12. The system of claim 11, wherein the system further comprises an initializer for assigning data of an MR spectrum to an interpreted data category or to a non-interpreted data category, wherein the initializer has an input for receiving MR data.

13. The system of claim 12, wherein the first expert system is a peak identifier and the second expert system is multiplet identifier.

14. The system of claim 13, further comprising a third expert system which is a structure analyzer and spectra matching system, wherein the structure analyzer and spectra matching system has a further input for receiving expected molecular structure information.

* * * * *